(12) United States Patent
Kleshinski et al.

(10) Patent No.: US 8,398,672 B2
(45) Date of Patent: *Mar. 19, 2013

(54) METHOD FOR ANCHORING A MEDICAL DEVICE

(75) Inventors: Stephen J. Kleshinski, San Jose, CA (US); Adrian Ravenscroft, Carver, MA (US)

(73) Assignee: Nitinol Devices and Components, Inc., Fremont, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 12/780,757

(22) Filed: May 14, 2010

(65) Prior Publication Data

US 2010/0222772 A1    Sep. 2, 2010

Related U.S. Application Data

(63) Continuation of application No. 12/625,941, filed on Nov. 25, 2009, which is a continuation of application No. 10/980,828, filed on Nov. 4, 2004, now abandoned, which is a continuation-in-part of application No. 10/705,226, filed on Nov. 12, 2003, now Pat. No. 7,056,286.

(51) Int. Cl.
*A61M 29/00*    (2006.01)
(52) U.S. Cl. ............ 606/200; 606/194; 606/198
(58) Field of Classification Search .......... 606/191, 606/200, 202, 194
See application file for complete search history.

(56) References Cited

U.S. PATENT DOCUMENTS

| | | |
|---|---|---|
| 3,593,854 A | 7/1971 | Swank |
| 3,659,593 A | 5/1972 | Vail |
| 3,765,536 A | 10/1973 | Rosenberg |
| 3,765,537 A | 10/1973 | Rosenberg |
| 3,788,328 A | 1/1974 | Alley et al. |
| 3,807,401 A | 4/1974 | Riggle et al. |
| 3,843,974 A | 10/1974 | Miller et al. |
| 3,874,388 A | 4/1975 | King et al. |
| 3,935,111 A | 1/1976 | Bentley |
| 3,952,747 A | 4/1976 | Kimmell, Jr. |
| 3,953,566 A | 4/1976 | Gore |
| 3,970,565 A | 7/1976 | Ahlstrand et al. |

(Continued)

FOREIGN PATENT DOCUMENTS

| | | |
|---|---|---|
| EP | 0362113 A1 | 4/1990 |
| EP | 0541063 A2 | 5/1993 |

(Continued)

OTHER PUBLICATIONS

Bonsignore et al.; U.S. Appl. No. 13/100,132 entitled "Alternating circumferential bridge stent design and methods for use therof," filed May 3, 2011.

(Continued)

*Primary Examiner* — Gary Jackson
*Assistant Examiner* — Diane Yabut
(74) *Attorney, Agent, or Firm* — Shay Glenn LLP

(57) ABSTRACT

A method and an apparatus for anchoring a medical implant device within a blood vessel or other body passageway are described herein. An anchor delivery system houses one or more expandable anchors connected to the medical implant device. The anchors remain housed in a non-expanded configuration until the medical implant device has been placed in a desired position within the body, and then the anchors are propelled through a body wall where each anchor expands outwardly from an anchor shaft. In one configuration, each anchor is formed as a compressible closed loop which extends outwardly from an anchor shaft and loops back to cross over and extend beyond the anchor shaft. To propel the anchors, a drive shaft is connected to a triggering unit which, when activated, causes the drive shaft to drive the anchor shafts in a direction such that the anchors are propelled through the body wall.

19 Claims, 8 Drawing Sheets

U.S. PATENT DOCUMENTS

| | | |
|---|---|---|
| 4,007,743 A | 2/1977 | Blake |
| 4,014,318 A | 3/1977 | Dockum et al. |
| 4,016,884 A | 4/1977 | Kwan-Gett |
| 4,073,723 A | 2/1978 | Swank et al. |
| 4,101,984 A | 7/1978 | MacGregor |
| 4,115,277 A | 9/1978 | Swank |
| 4,157,965 A | 6/1979 | Raible |
| 4,303,530 A | 12/1981 | Shah et al. |
| 4,319,580 A | 3/1982 | Colley et al. |
| 4,353,996 A | 10/1982 | Marconi et al. |
| 4,374,669 A | 2/1983 | Mac Gregor |
| 4,425,908 A | 1/1984 | Simon |
| 4,444,198 A | 4/1984 | Petre |
| 4,447,227 A | 5/1984 | Kotsanis |
| 4,457,487 A | 7/1984 | Steigerwald |
| 4,494,531 A | 1/1985 | Gianturco |
| 4,523,592 A | 6/1985 | Daniel |
| 4,542,748 A | 9/1985 | Roy |
| 4,565,823 A | 1/1986 | Ohata et al. |
| 4,586,501 A | 5/1986 | Claracq |
| 4,592,356 A | 6/1986 | Gutierrez |
| 4,616,656 A | 10/1986 | Nicholson et al. |
| 4,619,246 A | 10/1986 | Molgaard-Nielsen et al. |
| 4,627,836 A | 12/1986 | MacGregor |
| 4,642,089 A | 2/1987 | Zupkas et al. |
| 4,643,184 A | 2/1987 | Mobin-Uddin |
| 4,650,466 A | 3/1987 | Luther |
| 4,655,771 A | 4/1987 | Wallsten |
| 4,662,885 A | 5/1987 | DiPisa, Jr. |
| 4,664,682 A | 5/1987 | Monzen |
| 4,666,426 A | 5/1987 | Aigner |
| 4,666,543 A | 5/1987 | Kawano |
| 4,676,771 A | 6/1987 | Henke |
| 4,680,029 A | 7/1987 | Ranford et al. |
| 4,688,553 A | 8/1987 | Metals |
| 4,699,611 A | 10/1987 | Bowden |
| 4,722,724 A | 2/1988 | Schocket |
| 4,727,873 A | 3/1988 | Mobin-Uddin |
| 4,732,152 A | 3/1988 | Wallsten |
| 4,756,884 A | 7/1988 | Hillman et al. |
| 4,774,949 A | 10/1988 | Fogarty |
| 4,781,177 A | 11/1988 | Lebigot |
| 4,790,329 A | 12/1988 | Simon |
| 4,793,348 A | 12/1988 | Palmaz |
| 4,795,446 A | 1/1989 | Fecht |
| 4,817,600 A | 4/1989 | Herms et al. |
| 4,826,478 A | 5/1989 | Schocket |
| 4,828,563 A | 5/1989 | Muller-Lierheim |
| 4,832,055 A | 5/1989 | Palestrant |
| 4,858,623 A | 8/1989 | Bradshaw et al. |
| 4,873,978 A | 10/1989 | Ginsburg |
| 4,899,543 A | 2/1990 | Romanelli et al. |
| 4,917,089 A | 4/1990 | Sideris |
| 4,923,464 A | 5/1990 | DiPisa, Jr. |
| 4,944,727 A | 7/1990 | McCoy |
| 4,946,457 A | 8/1990 | Elliott |
| 4,954,251 A | 9/1990 | Barnes et al. |
| 4,957,501 A | 9/1990 | Lahille et al. |
| 4,969,891 A | 11/1990 | Gewertz |
| 4,969,902 A | 11/1990 | Ravo |
| 4,986,279 A | 1/1991 | O'Neill |
| 4,990,156 A | 2/1991 | Lefebvre |
| 5,018,530 A | 5/1991 | Rank et al. |
| 5,059,205 A | 10/1991 | El-Nounou et al. |
| 5,071,407 A | 12/1991 | Termin et al. |
| 5,092,996 A | 3/1992 | Spielberg |
| 5,102,417 A | 4/1992 | Palmaz |
| 5,108,407 A | 4/1992 | Geremia et al. |
| 5,108,418 A | 4/1992 | Lefebvre |
| 5,108,419 A | 4/1992 | Reger et al. |
| 5,108,420 A | 4/1992 | Marks |
| 5,127,916 A | 7/1992 | Spencer et al. |
| 5,133,733 A | 7/1992 | Rasmussen et al. |
| 5,147,379 A | 9/1992 | Sabbaghian et al. |
| 5,151,105 A | 9/1992 | Kwan-Gett |
| 5,152,777 A | 10/1992 | Goldberg et al. |
| 5,158,533 A | 10/1992 | Strauss et al. |
| 5,158,565 A | 10/1992 | Marcadis et al. |
| 5,171,259 A | 12/1992 | Inoue |
| 5,190,657 A | 3/1993 | Heagle et al. |
| 5,192,286 A | 3/1993 | Phan et al. |
| 5,192,301 A | 3/1993 | Kamiya et al. |
| 5,197,978 A | 3/1993 | Hess |
| 5,234,458 A | 8/1993 | Metais |
| 5,242,462 A * | 9/1993 | El-Nounou et al. .......... 606/200 |
| 5,257,621 A | 11/1993 | Bardy et al. |
| 5,269,924 A | 12/1993 | Rochat |
| 5,273,517 A | 12/1993 | Barone et al. |
| 5,282,823 A | 2/1994 | Schwartz et al. |
| 5,284,488 A | 2/1994 | Sideris |
| 5,300,086 A | 4/1994 | Gory et al. |
| 5,311,908 A | 5/1994 | Barone et al. |
| 5,334,217 A | 8/1994 | Das |
| 5,344,427 A | 9/1994 | Cottenceau et al. |
| 5,350,398 A | 9/1994 | Pavcnik et al. |
| 5,354,317 A | 10/1994 | Alt |
| 5,356,432 A | 10/1994 | Rutkow et al. |
| 5,366,504 A | 11/1994 | Andersen et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,421,832 A | 6/1995 | Lefebvre |
| 5,423,851 A | 6/1995 | Samuels |
| 5,425,744 A | 6/1995 | Fagan et al. |
| 5,433,727 A | 7/1995 | Sideris |
| 5,451,235 A | 9/1995 | Lock et al. |
| 5,464,449 A | 11/1995 | Ryan et al. |
| 5,466,216 A | 11/1995 | Brown et al. |
| 5,480,423 A | 1/1996 | Ravenscroft et al. |
| 5,484,424 A | 1/1996 | Cottenceau et al. |
| 5,486,193 A | 1/1996 | Bourne et al. |
| 5,503,801 A | 4/1996 | Brugger |
| 5,507,811 A | 4/1996 | Koike et al. |
| 5,522,881 A | 6/1996 | Lentz |
| 5,527,338 A | 6/1996 | Purdy |
| 5,531,788 A | 7/1996 | Dibie et al. |
| 5,545,206 A | 8/1996 | Carson |
| 5,549,626 A | 8/1996 | Miller et al. |
| 5,554,182 A | 9/1996 | Dinh et al. |
| 5,562,698 A | 10/1996 | Parker |
| 5,569,273 A | 10/1996 | Titone et al. |
| 5,571,166 A | 11/1996 | Dinh et al. |
| 5,578,045 A | 11/1996 | Das |
| 5,591,224 A | 1/1997 | Schwartz et al. |
| 5,591,227 A | 1/1997 | Dinh et al. |
| 5,591,251 A | 1/1997 | Brugger |
| 5,593,441 A | 1/1997 | Lichtenstein et al. |
| 5,595,909 A | 1/1997 | Hu et al. |
| 5,599,352 A | 2/1997 | Dinh et al. |
| 5,601,595 A | 2/1997 | Smith |
| 5,617,854 A | 4/1997 | Munsif |
| 5,626,599 A | 5/1997 | Bourne et al. |
| 5,626,605 A | 5/1997 | Irie et al. |
| 5,632,734 A | 5/1997 | Galel et al. |
| 5,634,474 A | 6/1997 | Grippi |
| 5,634,936 A | 6/1997 | Linden et al. |
| 5,634,942 A | 6/1997 | Chevillon et al. |
| 5,636,644 A | 6/1997 | Hart et al. |
| 5,637,097 A | 6/1997 | Yoon |
| 5,643,320 A | 7/1997 | Lower et al. |
| 5,643,321 A | 7/1997 | McDevitt |
| 5,649,950 A | 7/1997 | Bourne et al. |
| 5,653,747 A | 8/1997 | Dereume et al. |
| 5,653,755 A | 8/1997 | Ledergerber |
| 5,669,933 A | 9/1997 | Simon et al. |
| 5,672,585 A | 9/1997 | Pierschbacher et al. |
| 5,681,347 A | 10/1997 | Cathcart et al. |
| 5,695,518 A | 12/1997 | Laerum |
| 5,695,519 A | 12/1997 | Summers et al. |
| 5,702,421 A | 12/1997 | Schneidt |
| 5,704,910 A | 1/1998 | Humes |
| 5,709,704 A | 1/1998 | Nott et al. |
| 5,709,707 A | 1/1998 | Lock et al. |
| 5,713,853 A | 2/1998 | Clark et al. |
| 5,713,879 A | 2/1998 | Schneider |

| | | | | | | |
|---|---|---|---|---|---|---|
| 5,713,921 A | 2/1998 | Bonutti | | 6,051,014 A | 4/2000 | Jang |
| 5,716,408 A | 2/1998 | Eldridge et al. | | 6,053,932 A | 4/2000 | Daniel et al. |
| 5,718,717 A | 2/1998 | Bonutti | | 6,059,825 A | 5/2000 | Hobbs et al. |
| 5,720,764 A | 2/1998 | Naderlinger | | 6,068,645 A | 5/2000 | Tu |
| 5,722,964 A | 3/1998 | Herweck et al. | | 6,071,279 A | 6/2000 | Whayne et al. |
| 5,725,552 A | 3/1998 | Kotula et al. | | 6,077,281 A | 6/2000 | Das |
| 5,728,133 A | 3/1998 | Kontos | | 6,077,291 A | 6/2000 | Das |
| 5,733,294 A | 3/1998 | Forber et al. | | 6,080,178 A | 6/2000 | Meglin |
| 5,733,325 A | 3/1998 | Robinson et al. | | 6,080,182 A | 6/2000 | Shaw et al. |
| 5,735,892 A | 4/1998 | Myers et al. | | 6,090,096 A | 7/2000 | St. Goar et al. |
| 5,741,297 A | 4/1998 | Simon | | 6,090,097 A | 7/2000 | Barbut et al. |
| 5,755,663 A | 5/1998 | Larsen et al. | | 6,099,493 A | 8/2000 | Swisher |
| 5,755,778 A | 5/1998 | Kleshinski | | 6,099,549 A | 8/2000 | Bosma et al. |
| 5,755,790 A | 5/1998 | Chevillon et al. | | 6,117,105 A | 9/2000 | Bresnaham et al. |
| 5,766,246 A | 6/1998 | Mulhauser et al. | | 6,120,539 A | 9/2000 | Eldridge et al. |
| 5,772,668 A | 6/1998 | Summers et al. | | 6,123,715 A | 9/2000 | Amplatz |
| 5,788,661 A | 8/1998 | Japuntich | | 6,123,723 A | 9/2000 | Konya et al. |
| 5,792,179 A | 8/1998 | Sideris | | 6,129,755 A | 10/2000 | Mathis et al. |
| 5,795,322 A | 8/1998 | Boudewijn | | 6,142,987 A | 11/2000 | Tsugita |
| 5,795,325 A | 8/1998 | Valley et al. | | 6,146,404 A | 11/2000 | Kim et al. |
| 5,795,335 A | 8/1998 | Zinreich | | 6,152,946 A | 11/2000 | Broome et al. |
| 5,799,350 A | 9/1998 | Ferek-Petric et al. | | 6,171,328 B1 | 1/2001 | Addis |
| 5,800,457 A | 9/1998 | Gelbfish | | 6,171,329 B1 | 1/2001 | Shaw et al. |
| 5,800,507 A | 9/1998 | Schwartz | | 6,174,322 B1 | 1/2001 | Schneidt |
| 5,800,522 A | 9/1998 | Campbell et al. | | 6,200,276 B1 | 3/2001 | Biesel et al. |
| 5,824,034 A | 10/1998 | Schmitt et al. | | 6,206,888 B1 | 3/2001 | Bicek et al. |
| 5,827,229 A | 10/1998 | Auth et al. | | 6,214,020 B1 | 4/2001 | Mulhauser et al. |
| 5,830,224 A | 11/1998 | Cohn et al. | | 6,214,025 B1 | 4/2001 | Thistle et al. |
| 5,836,962 A | 11/1998 | Gianotti | | 6,214,029 B1 | 4/2001 | Thill et al. |
| 5,836,969 A | 11/1998 | Kim et al. | | 6,217,600 B1 | 4/2001 | DiMatteo |
| 5,843,167 A | 12/1998 | Dwyer et al. | | 6,221,092 B1 | 4/2001 | Koike et al. |
| 5,843,171 A | 12/1998 | Campbell et al. | | 6,231,581 B1 | 5/2001 | Shank et al. |
| 5,843,176 A | 12/1998 | Weier | | 6,231,589 B1 | 5/2001 | Wessman et al. |
| 5,846,261 A | 12/1998 | Kotula et al. | | 6,234,995 B1 | 5/2001 | Peacock, III |
| 5,849,004 A * | 12/1998 | Bramlet ............ 606/232 | | 6,235,044 B1 | 5/2001 | Root et al. |
| 5,849,034 A | 12/1998 | Schwartz | | 6,238,416 B1 | 5/2001 | Sideris |
| 5,853,420 A | 12/1998 | Chevillon et al. | | 6,241,727 B1 | 6/2001 | Tu et al. |
| 5,853,422 A | 12/1998 | Huebsch et al. | | 6,241,738 B1 | 6/2001 | Dereume et al. |
| 5,860,998 A | 1/1999 | Robinson et al. | | 6,245,012 B1 | 6/2001 | Kleshinski |
| 5,861,003 A | 1/1999 | Latson et al. | | 6,245,103 B1 | 6/2001 | Stinson |
| 5,871,693 A | 2/1999 | Lindsay | | 6,251,122 B1 | 6/2001 | Tsukernik |
| 5,873,906 A | 2/1999 | Lau et al. | | 6,258,026 B1 | 7/2001 | Ravenscroft et al. |
| 5,876,432 A | 3/1999 | Lau et al. | | 6,258,124 B1 | 7/2001 | Darois et al. |
| 5,879,366 A | 3/1999 | Shaw et al. | | 6,264,654 B1 | 7/2001 | Swartz et al. |
| 5,882,340 A | 3/1999 | Yoon | | 6,267,747 B1 | 7/2001 | Samson et al. |
| 5,882,351 A | 3/1999 | Fox | | 6,267,772 B1 | 7/2001 | Mulhauser et al. |
| 5,893,869 A | 4/1999 | Barnhart et al. | | 6,267,776 B1 | 7/2001 | O'Connell |
| 5,895,398 A | 4/1999 | Wensel et al. | | 6,267,777 B1 | 7/2001 | Bosma et al. |
| 5,904,703 A | 5/1999 | Gilson | | 6,270,515 B1 | 8/2001 | Linden et al. |
| 5,908,447 A | 6/1999 | Schroeppel et al. | | 6,273,901 B1 | 8/2001 | Whitcher et al. |
| 5,910,129 A | 6/1999 | Koblish et al. | | 6,277,139 B1 | 8/2001 | Levinson et al. |
| 5,925,074 A | 7/1999 | Gingras et al. | | 6,280,413 B1 | 8/2001 | Clark et al. |
| 5,928,261 A | 7/1999 | Ruiz | | 6,287,335 B1 | 9/2001 | Drasler et al. |
| 5,928,269 A | 7/1999 | Alt | | 6,311,692 B1 | 11/2001 | Vaska et al. |
| 5,938,683 A | 8/1999 | Lefebvre | | 6,325,815 B1 | 12/2001 | Kusleika et al. |
| 5,941,896 A | 8/1999 | Kerr | | 6,328,755 B1 | 12/2001 | Marshall |
| 5,947,995 A | 9/1999 | Samuels et al. | | 6,331,183 B1 | 12/2001 | Suon |
| 5,954,741 A | 9/1999 | Fox | | 6,334,864 B1 | 1/2002 | Amplatz et al. |
| 5,954,767 A | 9/1999 | Pajotin et al. | | 6,336,938 B1 | 1/2002 | Kavteladze et al. |
| 5,957,940 A | 9/1999 | Tanner et al. | | 6,340,364 B2 | 1/2002 | Kanesaka |
| 5,957,977 A | 9/1999 | Melvin | | 6,342,062 B1 | 1/2002 | Suon et al. |
| 5,965,089 A | 10/1999 | Jarvik et al. | | 6,342,063 B1 | 1/2002 | DeVries et al. |
| 5,967,976 A | 10/1999 | Larsen et al. | | 6,344,053 B1 | 2/2002 | Boneau |
| 5,968,053 A | 10/1999 | Revelas | | 6,355,052 B1 | 3/2002 | Neuss et al. |
| 5,968,071 A | 10/1999 | Chevillon et al. | | 6,358,230 B1 | 3/2002 | Davey |
| 5,976,172 A | 11/1999 | Homsma et al. | | 6,361,545 B1 | 3/2002 | Macoviak et al. |
| 5,980,558 A * | 11/1999 | Wiley ............ 606/232 | | 6,361,546 B1 | 3/2002 | Khosravi |
| 5,980,564 A | 11/1999 | Stinson | | 6,371,969 B1 | 4/2002 | Tsugita et al. |
| 5,984,917 A | 11/1999 | Fleischman et al. | | 6,371,971 B1 | 4/2002 | Tsugita et al. |
| 5,984,947 A | 11/1999 | Smith | | 6,379,368 B1 | 4/2002 | Corcoran et al. |
| 5,986,169 A | 11/1999 | Gjunter | | 6,391,044 B1 | 5/2002 | Yadav et al. |
| 5,991,657 A | 11/1999 | Kim | | 6,398,792 B1 | 6/2002 | O'Connor |
| 6,001,118 A | 12/1999 | Daniel et al. | | 6,402,736 B1 | 6/2002 | Brown et al. |
| 6,007,558 A * | 12/1999 | Ravenscroft et al. ....... 606/200 | | 6,416,293 B1 | 7/2002 | Bouchard et al. |
| 6,013,093 A | 1/2000 | Nott et al. | | 6,422,397 B1 | 7/2002 | Lynn et al. |
| 6,024,096 A | 2/2000 | Buckberg | | 6,428,559 B1 | 8/2002 | Johnson |
| 6,024,756 A | 2/2000 | Huebsch et al. | | 6,436,112 B2 | 8/2002 | Wensel et al. |
| 6,046,381 A | 4/2000 | Mucke et al. | | 6,436,120 B1 | 8/2002 | Meglin |
| 6,048,329 A | 4/2000 | Thompson et al. | | 6,436,121 B1 | 8/2002 | Blom |

| Patent | Kind | Date | Inventor |
|---|---|---|---|
| 6,440,077 | B1 | 8/2002 | Jung et al. |
| 6,440,152 | B1 | 8/2002 | Gainor et al. |
| 6,443,972 | B1 | 9/2002 | Bosma et al. |
| 6,447,530 | B1 | 9/2002 | Ostrovsky et al. |
| 6,451,257 | B1 | 9/2002 | Flamer |
| 6,454,775 | B1 | 9/2002 | Demarais et al. |
| 6,461,370 | B1 | 10/2002 | Gray et al. |
| 6,468,303 | B1 | 10/2002 | Amplatz et al. |
| 6,482,222 | B1 | 11/2002 | Bruckheimer et al. |
| 6,485,497 | B2 | 11/2002 | Wensel et al. |
| 6,485,502 | B2 | 11/2002 | Don Michael et al. |
| 6,488,692 | B1 | 12/2002 | Spence et al. |
| 6,491,712 | B1 | 12/2002 | O'Connor |
| 6,497,709 | B1 | 12/2002 | Heath |
| 6,506,204 | B2 | 1/2003 | Mazzocchi |
| 6,506,205 | B1 | 1/2003 | Goldberg et al. |
| 6,506,408 | B1 | 1/2003 | Palasis |
| 6,508,777 | B1 | 1/2003 | Macoviak et al. |
| 6,508,782 | B1 | 1/2003 | Evans et al. |
| 6,508,833 | B2 | 1/2003 | Pavcnik et al. |
| 6,517,559 | B1 | 2/2003 | O'Connell |
| 6,517,573 | B1 | 2/2003 | Pollock et al. |
| 6,527,962 | B1 | 3/2003 | Nadal |
| 6,533,805 | B1 | 3/2003 | Jervis |
| 6,534,035 | B1 | 3/2003 | Reed |
| 6,537,300 | B2 | 3/2003 | Girton |
| 6,540,767 | B1 | 4/2003 | Walak et al. |
| 6,540,768 | B1 | 4/2003 | Diaz et al. |
| 6,544,167 | B2 | 4/2003 | Buckberg et al. |
| 6,544,279 | B1 | 4/2003 | Hopkins et al. |
| 6,544,280 | B1 | 4/2003 | Daniel et al. |
| 6,547,754 | B1 | 4/2003 | Evans et al. |
| 6,551,303 | B1 | 4/2003 | Van Tassel et al. |
| 6,551,344 | B2 | 4/2003 | Thill |
| 6,562,071 | B2 | 5/2003 | Järvinen |
| 6,576,001 | B2 | 6/2003 | Werneth et al. |
| 6,582,447 | B1 | 6/2003 | Patel et al. |
| 6,585,689 | B1 | 7/2003 | Macoviak et al. |
| 6,585,756 | B1 | 7/2003 | Strecker |
| 6,592,546 | B1 | 7/2003 | Barbut et al. |
| 6,596,011 | B2 | 7/2003 | Johnson et al. |
| 6,596,013 | B2 | 7/2003 | Yang et al. |
| 6,602,272 | B2 | 8/2003 | Boylan et al. |
| 6,605,074 | B2 | 8/2003 | Zadno-Azizi et al. |
| 6,605,102 | B1 | 8/2003 | Mazzocchi et al. |
| 6,610,006 | B1 | 8/2003 | Amid et al. |
| 6,610,085 | B1 | 8/2003 | Lazarus |
| 6,613,076 | B1 | 9/2003 | Cherif-Cheikh |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,684 | B1 | 9/2003 | Vidlund et al. |
| 6,623,448 | B2 | 9/2003 | Slater |
| 6,623,506 | B2 | 9/2003 | McGuckin, Jr. et al. |
| 6,623,507 | B2 | 9/2003 | Saleh |
| 6,626,899 | B2 | 9/2003 | Houser et al. |
| 6,626,937 | B1 | 9/2003 | Cox |
| 6,635,070 | B2 | 10/2003 | Evans et al. |
| 6,638,259 | B1 | 10/2003 | Palasis et al. |
| 6,645,143 | B2 | 11/2003 | VanTassel et al. |
| 6,645,152 | B1 | 11/2003 | Jung et al. |
| 6,645,202 | B1 | 11/2003 | Pless et al. |
| 6,645,225 | B1 | 11/2003 | Atkinson |
| 6,652,554 | B1 | 11/2003 | Wholey et al. |
| 6,652,555 | B1 | 11/2003 | VanTassel et al. |
| 6,652,556 | B1 | 11/2003 | VanTassel et al. |
| 6,656,203 | B2 | 12/2003 | Roth et al. |
| 6,656,206 | B2 | 12/2003 | Corcoran et al. |
| 6,656,221 | B2 | 12/2003 | Taylor et al. |
| 6,660,021 | B1 | 12/2003 | Palmer et al. |
| 6,660,031 | B2 | 12/2003 | Tran et al. |
| 6,663,606 | B1 | 12/2003 | Barry et al. |
| 6,663,651 | B2 | 12/2003 | Krolik et al. |
| 6,669,708 | B1 | 12/2003 | Nissenbaum et al. |
| 6,673,102 | B1 | 1/2004 | Vonesh et al. |
| 6,676,666 | B2 | 1/2004 | Vrba et al. |
| 6,676,682 | B1 | 1/2004 | Tsugita et al. |
| 6,682,505 | B2 | 1/2004 | Bates et al. |
| 6,685,738 | B2 | 2/2004 | Chouinard et al. |
| 6,689,150 | B1 | 2/2004 | VanTassel et al. |
| 6,692,459 | B2 | 2/2004 | Teitelbaum |
| 6,692,508 | B2 | 2/2004 | Wensel et al. |
| 6,692,509 | B2 | 2/2004 | Wensel et al. |
| 6,694,983 | B2 | 2/2004 | Wolf et al. |
| 6,695,858 | B1 | 2/2004 | Dubrul et al. |
| 6,695,864 | B2 | 2/2004 | Macoviak et al. |
| 6,702,835 | B2 | 3/2004 | Ginn |
| 6,706,065 | B2 | 3/2004 | Langberg et al. |
| 6,709,442 | B2 | 3/2004 | Miller et al. |
| 6,712,834 | B2 | 3/2004 | Yassour et al. |
| 6,712,835 | B2 | 3/2004 | Mazzocchi et al. |
| 6,712,836 | B1 | 3/2004 | Berg et al. |
| 6,716,238 | B2 | 4/2004 | Elliott |
| 6,723,133 | B1 | 4/2004 | Pajotin |
| 6,726,701 | B2 | 4/2004 | Gilson et al. |
| 6,726,703 | B2 | 4/2004 | Broome et al. |
| 6,731,982 | B1 | 5/2004 | Kroll et al. |
| 6,736,823 | B2 | 5/2004 | Darois et al. |
| 6,736,839 | B2 | 5/2004 | Cummings |
| 6,736,854 | B2 | 5/2004 | Vadurro et al. |
| 6,740,061 | B1 | 5/2004 | Oslund et al. |
| 6,740,094 | B2 | 5/2004 | Maitland et al. |
| 6,740,112 | B2 | 5/2004 | Yodfat et al. |
| 6,740,122 | B1 | 5/2004 | Pajotin |
| 6,752,825 | B2 | 6/2004 | Eskuri |
| 6,754,528 | B2 | 6/2004 | Bardy et al. |
| 6,754,531 | B1 | 6/2004 | Kroll et al. |
| 6,755,846 | B1 | 6/2004 | Yadav |
| 6,755,847 | B2 | 6/2004 | Eskuri |
| 6,756,094 | B1 | 6/2004 | Wang et al. |
| 6,758,830 | B1 | 7/2004 | Schaer et al. |
| 6,764,510 | B2 | 7/2004 | Vidlund et al. |
| 6,766,196 | B1 | 7/2004 | Kroll et al. |
| 6,776,770 | B1 | 8/2004 | Trerotola |
| 6,776,784 | B2 | 8/2004 | Ginn |
| 6,780,183 | B2 | 8/2004 | Jimenez, Jr. et al. |
| 6,783,499 | B2 | 8/2004 | Schwartz |
| 6,783,538 | B2 | 8/2004 | McGuckin, Jr. et al. |
| 6,790,213 | B2 | 9/2004 | Cherok et al. |
| 6,790,218 | B2 | 9/2004 | Jayaraman |
| 6,790,230 | B2 | 9/2004 | Beyersdorf et al. |
| 6,790,231 | B2 | 9/2004 | Liddicoat et al. |
| 6,793,666 | B2 | 9/2004 | Hansen et al. |
| 6,795,731 | B1 | 9/2004 | Kroll et al. |
| 6,797,083 | B2 | 9/2004 | Peterson |
| 6,799,357 | B2 | 10/2004 | Webb et al. |
| 6,805,128 | B1 | 10/2004 | Pless et al. |
| 6,805,129 | B1 | 10/2004 | Pless et al. |
| 6,805,711 | B2 | 10/2004 | Quijano et al. |
| 6,808,537 | B2 | 10/2004 | Michelson |
| 6,827,731 | B2 | 12/2004 | Armstrong et al. |
| 6,835,378 | B2 | 12/2004 | Davis et al. |
| 6,840,950 | B2 | 1/2005 | Stanford et al. |
| 6,843,798 | B2 | 1/2005 | Kusleika et al. |
| 6,866,662 | B2 | 3/2005 | Fuimaono et al. |
| 6,866,680 | B2 | 3/2005 | Yassour et al. |
| 6,881,218 | B2 | 4/2005 | Beyer et al. |
| 6,887,214 | B1 | 5/2005 | Levin et al. |
| 6,887,257 | B2 | 5/2005 | Salahieh et al. |
| 6,887,268 | B2 | 5/2005 | Butaric et al. |
| 6,890,353 | B2 | 5/2005 | Cohn et al. |
| 6,895,265 | B2 | 5/2005 | Silver |
| 6,899,727 | B2 | 5/2005 | Armstrong et al. |
| 6,902,572 | B2 | 6/2005 | Beulke et al. |
| 6,905,479 | B1 | 6/2005 | Bouchard et al. |
| 6,907,286 | B1 | 6/2005 | Kroll et al. |
| 6,911,037 | B2 | 6/2005 | Gainor et al. |
| 6,913,614 | B2 | 7/2005 | Marino et al. |
| 6,913,622 | B2 | 7/2005 | Gjunter |
| 6,929,633 | B2 | 8/2005 | Evans et al. |
| 6,931,280 | B1 | 8/2005 | Yang |
| 6,939,361 | B1 | 9/2005 | Kleshinski |
| 6,942,635 | B2 | 9/2005 | Rosenblatt et al. |
| 6,951,570 | B2 | 10/2005 | Linder et al. |
| 6,962,598 | B2 | 11/2005 | Linder et al. |
| 6,966,886 | B2 | 11/2005 | Appling |
| 6,972,025 | B2 | 12/2005 | WasDyke |
| 6,974,469 | B2 | 12/2005 | Broome et al. |

| | | |
|---|---|---|
| 6,976,967 B2 | 12/2005 | Dahl et al. |
| 6,988,983 B2 | 1/2006 | Connors et al. |
| 6,989,021 B2 | 1/2006 | Bosma et al. |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,004,964 B2 | 2/2006 | Thompson et al. |
| 7,011,671 B2 | 3/2006 | Welch |
| 7,012,106 B2 | 3/2006 | Yuan et al. |
| 7,014,765 B2 | 3/2006 | Dannenmaier |
| 7,052,487 B2 | 5/2006 | Cohn et al. |
| 7,052,500 B2 | 5/2006 | Bashiri et al. |
| 7,052,511 B2 | 5/2006 | Weldon et al. |
| 7,056,286 B2 | 6/2006 | Ravenscroft et al. |
| 7,056,336 B2 | 6/2006 | Armstrong et al. |
| 7,060,082 B2 | 6/2006 | Goll et al. |
| 7,063,682 B1 | 6/2006 | Whayne et al. |
| 7,066,951 B2 | 6/2006 | Chobotov |
| 7,083,633 B2 | 8/2006 | Morrill et al. |
| 7,087,069 B2 | 8/2006 | Petrovic et al. |
| 7,094,249 B1 | 8/2006 | Broome et al. |
| 7,112,219 B2 | 9/2006 | Vidlund et al. |
| 7,122,034 B2 | 10/2006 | Belhe et al. |
| 7,125,420 B2 | 10/2006 | Rourke et al. |
| 7,131,966 B1 | 11/2006 | Tamari |
| 7,137,991 B2 | 11/2006 | Fedie |
| 7,147,649 B2 | 12/2006 | Thomas |
| 7,149,587 B2 | 12/2006 | Wardle et al. |
| 7,152,452 B2 | 12/2006 | Kokish |
| 7,169,165 B2 | 1/2007 | Belef et al. |
| 7,179,274 B2 | 2/2007 | Bruckheimer et al. |
| 7,179,275 B2 | 2/2007 | McGuckin, Jr. et al. |
| 7,179,291 B2 | 2/2007 | Rourke et al. |
| 7,181,261 B2 | 2/2007 | Silver et al. |
| 7,186,262 B2 | 3/2007 | Saadat |
| 7,186,264 B2 | 3/2007 | Liddicoat et al. |
| 7,189,203 B2 | 3/2007 | Lau et al. |
| 7,192,434 B2 | 3/2007 | Anderson et al. |
| 7,209,783 B2 | 4/2007 | Fellows et al. |
| 7,214,237 B2 | 5/2007 | Don Michael et al. |
| 7,220,271 B2 | 5/2007 | Clubb et al. |
| 7,226,464 B2 | 6/2007 | Garner et al. |
| 7,229,462 B2 | 6/2007 | Sutton et al. |
| 7,229,469 B1 | 6/2007 | Witzel et al. |
| 7,231,260 B2 | 6/2007 | Wallace et al. |
| 7,232,453 B2 | 6/2007 | Shimon |
| 7,241,257 B1 | 7/2007 | Ainsworth et al. |
| 7,241,310 B2 | 7/2007 | Taylor et al. |
| 7,250,049 B2 | 7/2007 | Roop et al. |
| 7,258,697 B1 | 8/2007 | Cox et al. |
| 7,285,119 B2 | 10/2007 | Stewart et al. |
| 7,294,214 B2 | 11/2007 | Craig |
| 7,294,311 B2 | 11/2007 | Coville |
| 7,303,560 B2 | 12/2007 | Chin et al. |
| 7,306,618 B2 | 12/2007 | Demond et al. |
| 7,306,622 B2 | 12/2007 | Jones et al. |
| 7,309,354 B2 | 12/2007 | Mathis et al. |
| 7,316,708 B2 | 1/2008 | Gordon et al. |
| 7,319,035 B2 | 1/2008 | Vacanti et al. |
| 7,323,001 B2 | 1/2008 | Clubb et al. |
| 7,323,002 B2 | 1/2008 | Johnson et al. |
| 7,323,003 B2 | 1/2008 | Lowe |
| 7,329,269 B2 | 2/2008 | Shapiro et al. |
| 7,331,976 B2 | 2/2008 | McGuckin, Jr. et al. |
| 7,331,992 B2 | 2/2008 | Randall et al. |
| 7,338,512 B2 | 3/2008 | McGuckin, Jr. et al. |
| 7,344,553 B2 | 3/2008 | Opolski et al. |
| 7,351,259 B2 | 4/2008 | Swinford et al. |
| 7,357,812 B2 | 4/2008 | Andreas et al. |
| 7,364,588 B2 | 4/2008 | Mathis et al. |
| 7,399,308 B2 | 7/2008 | Borillo et al. |
| 7,431,691 B1 | 10/2008 | Wilk |
| 7,445,630 B2 | 11/2008 | Lashinski et al. |
| 7,452,371 B2 | 11/2008 | Pavcnik et al. |
| 7,594,927 B2 | 9/2009 | Majercak et al. |
| 7,604,870 B2 | 10/2009 | Chernyshov et al. |
| 7,883,538 B2 * | 2/2011 | To et al. .......... 623/2.11 |
| 2001/0039434 A1 | 11/2001 | Frazier |
| 2002/0169474 A1 | 11/2002 | Kusleika et al. |
| 2002/0183787 A1 | 12/2002 | Wahr et al. |
| 2003/0028213 A1 | 2/2003 | Thill et al. |
| 2003/0144694 A1 | 7/2003 | Chanduszko et al. |
| 2003/0167068 A1 | 9/2003 | Amplatz |
| 2003/0191495 A1 | 10/2003 | Ryan et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |
| 2004/0039442 A1 | 2/2004 | St. Goar et al. |
| 2004/0073242 A1 | 4/2004 | Chanduszko |
| 2004/0092973 A1 | 5/2004 | Chanduszko et al. |
| 2004/0093017 A1 | 5/2004 | Chanduszko |
| 2004/0102807 A1 | 5/2004 | Kusleika et al. |
| 2004/0133236 A1 | 7/2004 | Chanduszko |
| 2004/0167609 A1 | 8/2004 | Majercak |
| 2004/0176799 A1 | 9/2004 | Chanduszko et al. |
| 2004/0215219 A1 | 10/2004 | Eldridge et al. |
| 2004/0249408 A1 | 12/2004 | Murphy et al. |
| 2004/0267191 A1 | 12/2004 | Gifford, III et al. |
| 2004/0267306 A1 | 12/2004 | Blaeser et al. |
| 2005/0043759 A1 | 2/2005 | Chanduszko |
| 2005/0055080 A1 | 3/2005 | Istephanous et al. |
| 2005/0090857 A1 | 4/2005 | Kusleika et al. |
| 2005/0090858 A1 | 4/2005 | Pavlovic |
| 2005/0131451 A1 | 6/2005 | Kleshinski et al. |
| 2005/0192620 A1 | 9/2005 | Cully et al. |
| 2005/0192626 A1 | 9/2005 | Widomski et al. |
| 2005/0192654 A1 | 9/2005 | Chanduszko et al. |
| 2005/0197186 A1 | 9/2005 | Ohta |
| 2005/0197187 A1 | 9/2005 | Mitsuyoshi et al. |
| 2005/0216054 A1 | 9/2005 | Widomski et al. |
| 2006/0015137 A1 | 1/2006 | WasDyke |
| 2006/0106452 A1 | 5/2006 | Niermann |
| 2008/0208319 A1 | 8/2008 | Rabkin et al. |
| 2010/0776545 | 4/2010 | Wu et al. |

FOREIGN PATENT DOCUMENTS

| | | |
|---|---|---|
| EP | 0621016 A1 | 10/1993 |
| EP | 0657147 A2 | 6/1995 |
| EP | 0701800 A1 | 3/1996 |
| EP | 0962194 A2 | 12/1999 |
| EP | 1050265 A2 | 11/2000 |
| JP | 06189971 A2 | 7/1994 |
| JP | 06343703 A2 | 12/1994 |
| JP | 07265339 A2 | 10/1995 |
| JP | 08089585 A2 | 4/1996 |
| JP | 08215200 | 8/1996 |
| JP | 08257031 | 10/1996 |
| JP | 08299456 A2 | 11/1996 |
| JP | 2000126304 A | 5/2000 |
| JP | 2002119516 A | 4/2002 |
| JP | 2002525183 | 8/2002 |
| JP | 2002355248 A | 12/2002 |
| JP | 2003521308 | 7/2003 |
| JP | 2003521988 | 7/2003 |
| JP | 2003523805 | 8/2003 |
| WO | WO97/13463 A1 | 4/1997 |
| WO | WO03/101312 A1 | 12/2003 |

OTHER PUBLICATIONS

Bonsignore et al.; U.S. Appl. No. 12/939,894 entitled "Alternating circumferenctial bridge stent design and methods for use thereof," filed Nov. 4, 2010.

Duerig et al.; An overview of superelastic stent design; Min Invas Ther & Allied Technol; vol. 9(3/4); pp. 235-246; 2000.

* cited by examiner

FIG. 10
FIG. 9
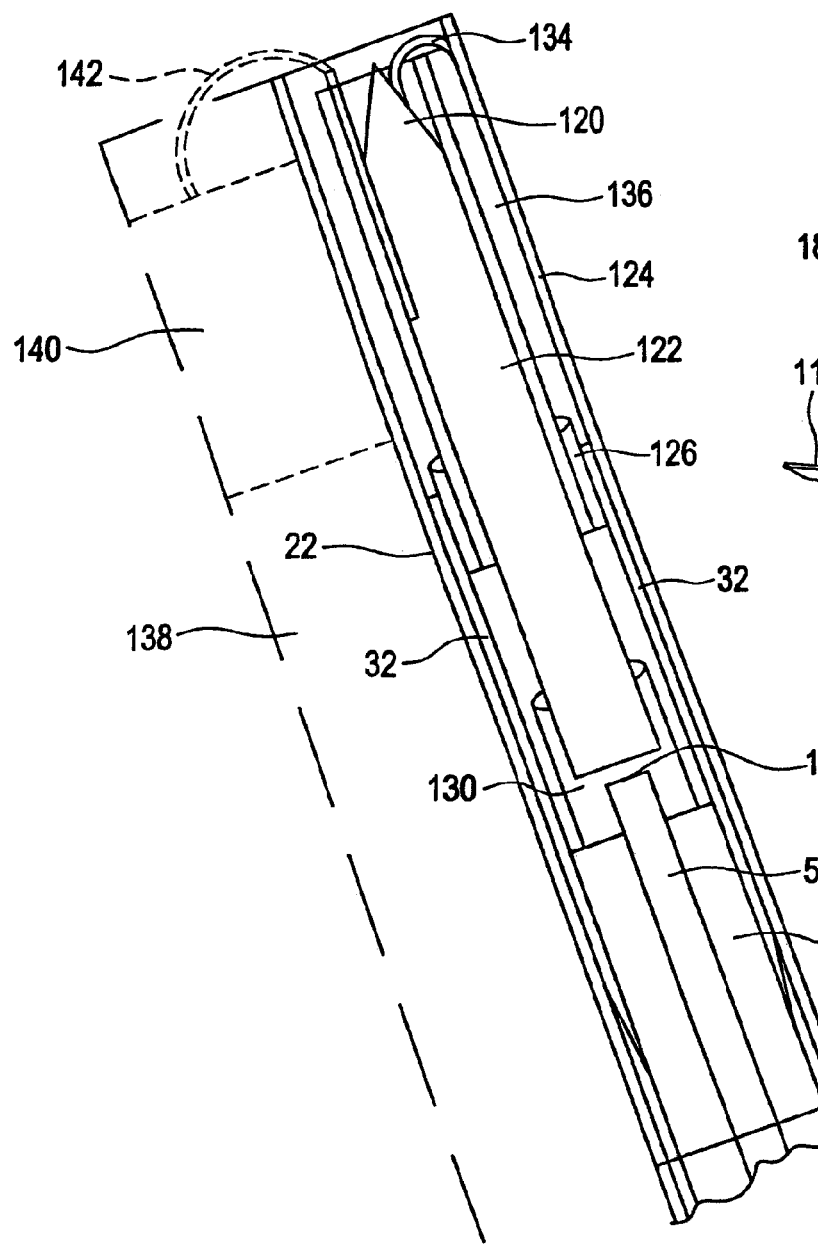
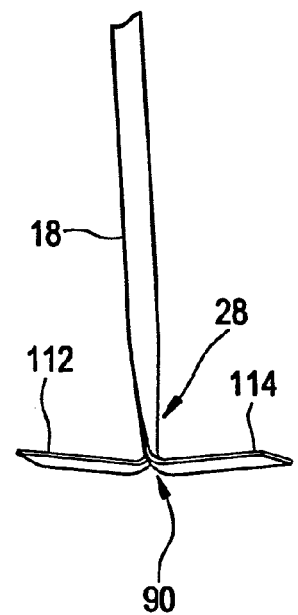

METHOD FOR ANCHORING A MEDICAL DEVICE

CROSS REFERENCE TO RELATED APPLICATIONS

This application is a continuation of U.S. patent application Ser. No. 12/625,941, filed Nov. 25, 2009 entitled "MEDICAL DEVICE ANCHOR AND DELIVERY SYSTEM", which is a continuation of U.S. patent application Ser. No. 10/980,828, filed Nov. 4, 2004 now abandoned, entitled "MEDICAL DEVICE ANCHOR AND DELIVERY SYSTEM", which is a continuation-in-part of U.S. patent application Ser. No. 10/705,226, filed Nov. 12, 2003 entitled "MEDICAL DEVICE ANCHOR AND DELIVERY SYSTEM", now U.S. Pat. No. 7,056,286.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Recent advances in medical technology have resulted in the development of a variety of medical devices for permanent or temporary implantation in the human body. Effective positioning of such devices can prove to be a very difficult task, and maintaining an implanted device in a desired position for an extended period of time is often more difficult. This is particularly true if the implanted device is to remain only temporarily and is designed to facilitate subsequent removal.

A number of medical implant devices are designed to collapse for insertion within a catheter or other delivery unit and to expand to a predetermined shape when ejected after delivery. Many of these self expanding devices rely primarily upon the contact between the device and the wall of a body vessel or passageway to maintain the device in position after the delivery unit is removed. Unfortunately, changes in the dimensions of the body vessel or passageway or variations in the flow of blood or other fluids there through can cause the medical implant to migrate and change position.

It is extremely important that a medical implant device be properly positioned and oriented, and that this position and orientation be maintained. Otherwise, effective performance of such therapeutic devices will not be achieved. It is often very difficult to move such a device into position with the desired orientation, and once this is achieved, it is critical that no further motion occur.

In an attempt to prevent migration of a medical implant device, rigid hooks are often formed on the device to engage the wall of a body vessel or passageway as the implant device expands into contact with the wall. After a few weeks, the endothelium layer grows over rigid hooks which will not easily bend under the influence of withdrawal pressure, and the medical implant device will be locked in place by the embedded hooks. This may be acceptable for a permanent implant, but rigid hooks are not a viable option if the medical implant device is to be removed after several weeks or months.

To facilitate removal of a previously implanted medical device by withdrawal of the anchoring hooks from an enveloping endothelium layer without risking substantial damage to the wall of a body vessel or passageway, the hooks have been formed to straighten when subjected to a withdrawal force greater than a maximum migration force. U.S. Pat. Nos. 6,007,558 and 6,258,026 to Ravenscroft, et al show hooks which are formed to bend and straighten in response to a withdrawal force, while U.S. Pat. No. 4,425,908 to Simon, U.S. Pat. No. 4,817,600 to Herms, et al, U.S. Pat. No. 5,108,418 to Lefebvre, U.S. Pat. No. 5,133,733 to Rasmussen, et al, U.S. Pat. No. 5,242,462 to El-Nounou, et al, U.S. Pat. No. 5,370,657 to Irie, U.S. Pat. No. 5,601,595 to Smith, U.S. Pat. No. 5,800,457 to Gelbfish, and U.S. Pat. No. 5,853,420 to Chevillon, et al all disclose expandable medical implant devices; many with anchoring hooks.

Anchoring hooks, although effective in many instances, are subject to a number of disadvantages which can make it difficult to properly position and maintain the position of a medical implant device. In prior devices, the anchoring hooks are engaged due to the expansion of the device into contact with the wall of a body vessel or passageway, and if the device moves from a desired position during expansion and contact with the wall occurs, the device cannot be easily repositioned. The anchoring function of the hooks is not separable from the expansion of the device.

In cases where the operation of the hooks is tied to the expansion of a medical implant device, there can be instances where one or more of the hooks fails to properly engage the wall of a body vessel or passageway causing the device to become off center. Sometimes movement of the device longitudinally will engage the errant hooks, but this movement can also alter the position of the device.

Also, the configuration of a hook which curves in a single direction from a shaft to a pointed end can prove to be a disadvantage. When hooks are used to anchor a medical implant device within a blood vessel, it is important that the hook be oriented to curve in the direction of normal blood flow through the vessel as it engages the vessel wall. Thus when engaged, the hook will extend from the shaft toward the point substantially in the direction of the longitudinal axis of the blood vessel, and will effectively resist migration of the medical implant device in response to pressure thereon from blood flow in the normal direction through the blood vessel. However, there are conditions which can result in a backflow of blood in a blood vessel, and pressure on the device and the anchoring hooks resulting from such backflow can cause the hooks to back out and disengage from the vessel, thus changing the orientation of the device within the blood vessel and causing deleterious changes in the performance of the implant.

Finally, even if the hooks of an implant device are properly engaged with a vessel wall, there are conditions which result in the subsequent outward expansion of the vessel wall to an extent where the hooks tend to become disengaged.

SUMMARY OF THE INVENTION

It is a primary object of the present invention to provide a novel and improved method for positioning and anchoring a medical implant device which includes positively propelling one or more anchors through a body wall subsequent to a medical implant device connected to the anchor reaching a desired position and coming to rest.

Another object of the present invention is to provide a novel and improved medical device anchor and delivery system wherein one or more anchors are positively propelled through a body wall. Once an anchor has passed through the wall, it expands outwardly from at least two opposed sides of an anchor shaft.

An additional object of the present invention is to provide a novel and improved medical device anchor designed to penetrate a body wall from a first side to a second side and to expand outwardly from at least two opposed sides of an anchor shaft after penetration.

Another object of the present invention is to provide a novel and improved medical device anchor designed to penetrate the wall of a body vessel from a first side to a second side and to expand outwardly from an anchor shaft in a unique manner after penetration. The expanded anchor is designed to be loaded in compression against the second wall of the vessel and to change in configuration to increase the anchoring function provided thereby in response to forces applied thereto at an angle to the longitudinal axis of the vessel.

Yet another object of the present invention is to provide a novel and improved medical device anchor designed to penetrate the wall of a body vessel from a first side to a second side and to expand outwardly from an anchor shaft in a unique manner after penetration. The anchor expands outwardly from the anchor shaft into one or more loops with each loop curving back to cross the anchor shaft. The section of the loop which crosses the anchor shaft is formed to engage the second wall of the vessel and to load the anchor in compression against the second wall of the vessel in response to forces which are applied to a medical device attached to the anchor or which result from expansion of the vessel wall.

A further object of the present invention is to provide a novel and improved medical device anchor and delivery system wherein one or more anchors are positively propelled through a body wall subsequent to a medical implant device connected to the anchors reaching a desired position and coming to rest. The anchor delivery system facilitates removal and reinsertion of the anchors without requiring that the medical implant device connected thereto be compressed and/or removed.

Yet another object of the present invention is to provide a novel and improved anchor and anchor delivery system for a medical implant device to anchor the device in position within a blood vessel or other body passageway. Once the medical implant device has been positioned and expanded into contact with the wall of the blood vessel or body passageway, the anchor delivery system then positively propels one or more anchors through the vessel or passageway wall where the anchors expand outwardly on opposite sides of an anchor shaft. The anchor delivery system permits the anchors to be withdrawn and then reinserted through the wall without the necessity to collapse the medical implant device.

A further object of the present invention is to provide a novel and improved anchor and anchor delivery system for a medical implant device to anchor the device in position within a blood vessel or other body passageway while facilitating the subsequent withdrawal of the device. The anchor delivery system positively propels one or more anchors through the wall of a blood vessel or body passageway once the medical implant device has expanded into contact with the wall, and the anchors then expand outwardly from opposite sides of an anchor shaft. The anchors are formed to contract back toward the longitudinal axis of the anchor shaft in response to a predetermined force to permit withdrawal through the wall.

A still further object of the present invention is to provide a novel and improved anchor and anchor delivery system for a blood clot filter where the delivery system includes elongate, tubular filter legs which house the anchors. Once the filter legs are ejected from a catheter or delivery tube and expand into contact with the blood vessel wall, the anchor delivery system positively propels the anchors outwardly from the filter legs and through the blood vessel wall from a first side to a second side where the anchors expand outwardly from an anchor shaft against the second side of the wall. Each anchor is formed to contract back toward the longitudinal axis of its anchor shaft in response to a predetermined force to permit withdrawal through the wall, and this permits the anchors to be withdrawn back into the filter legs and then again propelled through the blood vessel wall without collapsing the filter legs.

Yet a further object of the present invention is to provide a novel and improved anchor delivery system for a blood clot filter where the delivery system includes elongate, tubular filter legs which house the anchors and which expand into contact with a blood vessel wall. A side opening is formed in the portion of the filter leg which will contact the blood vessel wall, and the filter leg is designed to facilitate ejection of the anchor through the side opening transverse to the filter leg. Once the filter legs expand into contact with the blood vessel wall, the anchor delivery system positively propels the anchors laterally outward from the side openings in the filter legs and through the blood vessel wall from a first side to a second side where the anchors expand outwardly from an anchor shaft against the second side of the blood vessel wall.

These and other objects of the present invention are achieved by providing an anchor delivery system which houses one or more uniquely configured anchors which are connected to a medical implant device. The anchors remain housed until after the medical implant device has come to rest in a desired position within a body, and then the anchors are positively propelled through a body wall from a first side to a second side where each anchor expands from a single shaft configuration. To propel the anchors, a drive shaft extends from an anchor support sleeve back to a triggering unit which, when activated, causes the drive shaft to move the anchor support sleeve in a direction to propel the anchors through the body wall. The triggering unit may be spring powered or solenoid powered.

BRIEF DESCRIPTION OF THE DRAWINGS

FIG. 9 is a perspective view of a third embodiment of a deployed anchor of the present invention;

FIG. 10 is a sectional view of a single anchor and anchor delivery system of the present invention;

DETAILED DESCRIPTION OF THE INVENTION

Figure 1:
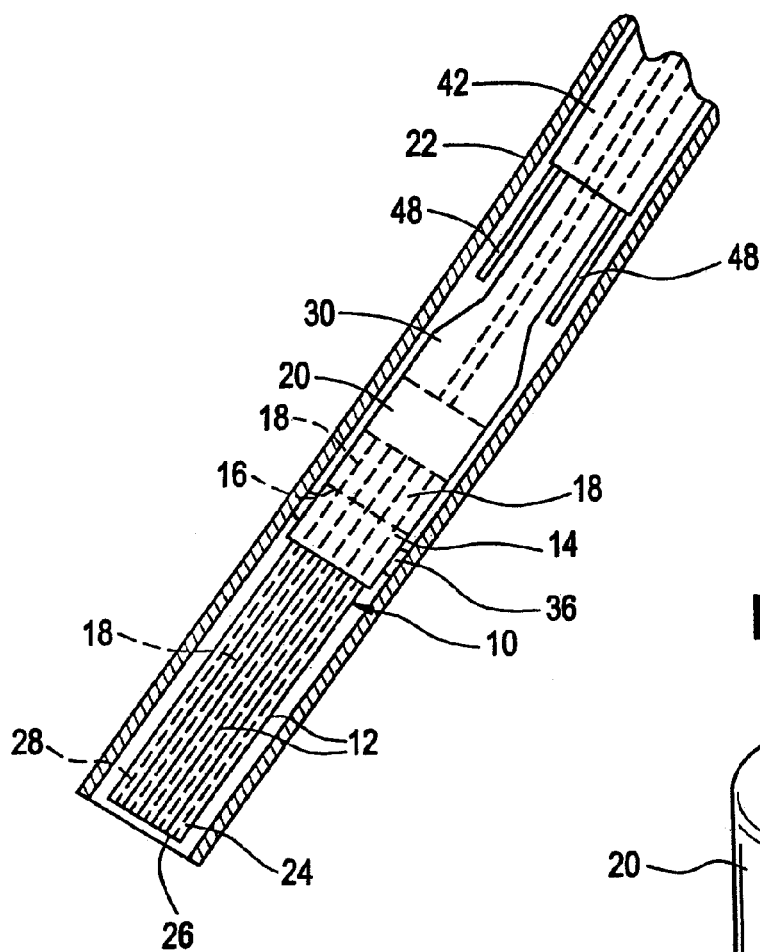
FIG. 1 is a sectional view showing a blood clot filter with anchors formed in accordance with the present invention mounted within a catheter.
Figure 2:
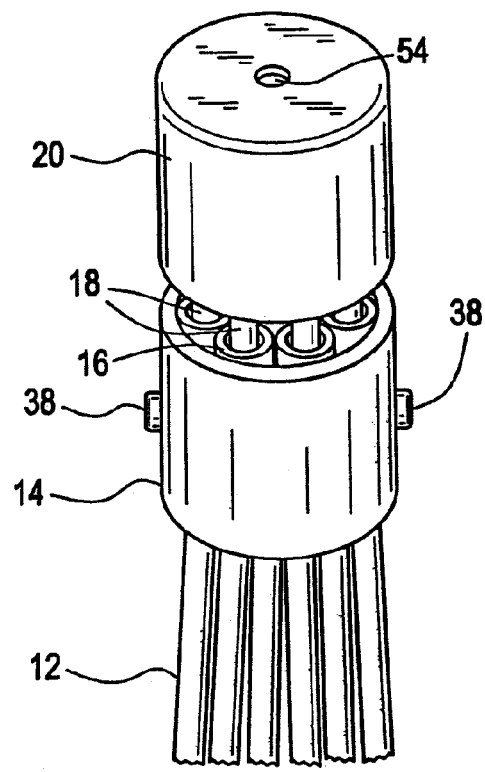
FIG. 2 is a perspective view showing the anchor support hub and leg retention sleeve of FIG. 1.

Referring to FIGS. 1-2, a blood clot filter which includes anchors in accordance with the present invention is illustrated generally at 10. This filter, shown for illustration as a vena cava filter, is formed with a plurality of elongate legs 12 which are secured to, and extend outwardly from a leg retention sleeve 14. The elongate legs are formed by small, open ended tubes each having a first open end 16 which opens at the leg retention sleeve. A plurality of long anchor shafts 18 are attached at a distal end to an anchor support hub 20 which is spaced from the leg retention sleeve when the vena cava filter is collapsed within a catheter or delivery tube 22. Each shaft 18 extends from the anchor support hub 20 into the first open end 16 of a tubular leg 12 and through the leg to a distal end 24 at a point adjacent to a second open end 26 of the tubular leg. An anchor 28 is formed at the distal end of each shaft 18 in a manner to be described.

Figure 6:
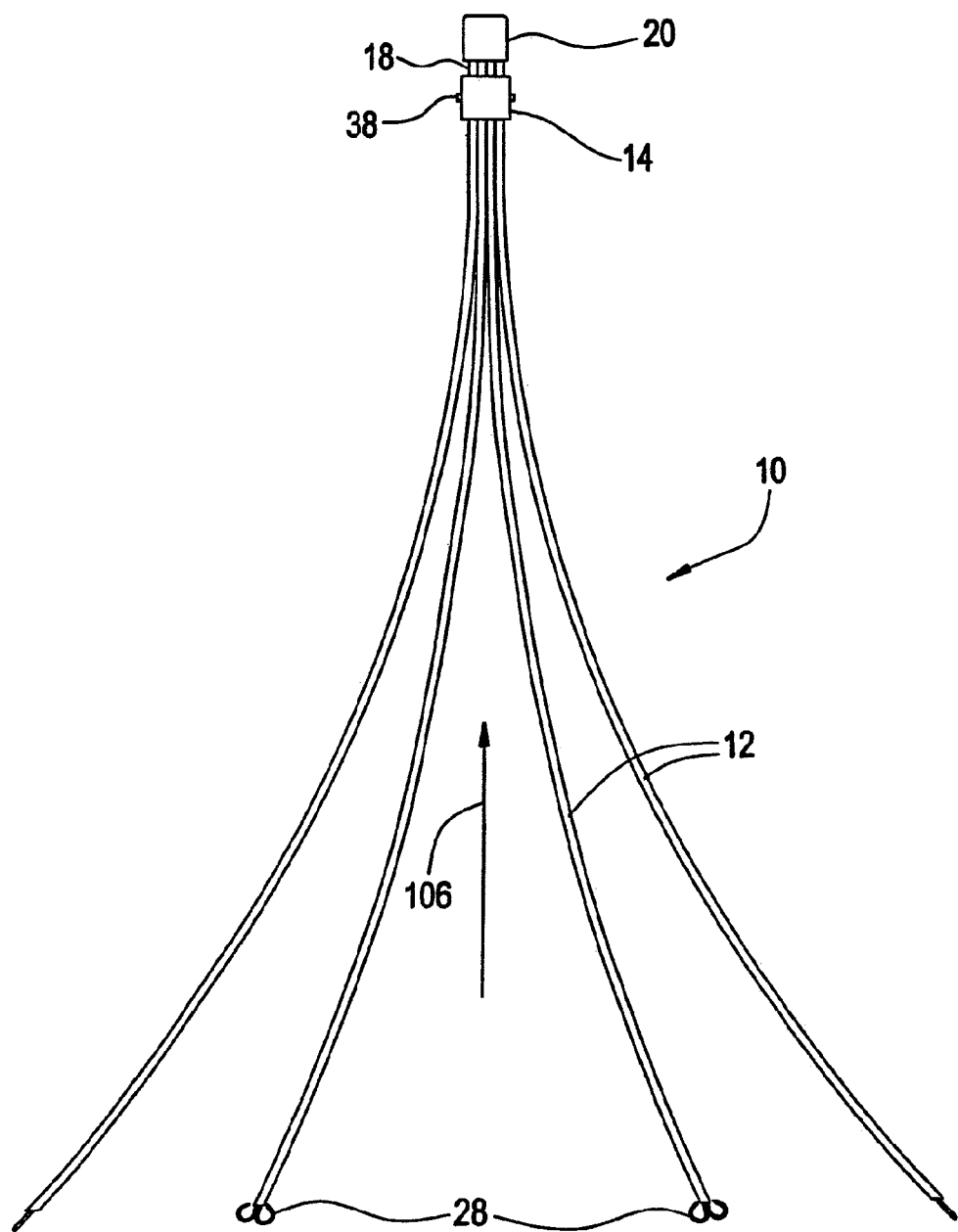
FIG. 6 is a perspective view of the deployed blood clot filter of FIG. 1.

The elongate legs 12 and the long anchor shafts 18 are formed of a material which will permit them to be compressed toward the longitudinal axis of the filter 10 for delivery by a catheter 22. Once the filter is ejected from the catheter, the legs 12 and the shafts 18 are designed to expand outwardly from the filter longitudinal axis as shown in FIG. 6 to bring the legs into contact with the wall of a blood vessel. Although spring metal and suitable plastics can be used to form the legs 12 and/or the shafts 18, it is preferable to form the anchor shafts 18 and in most cases the legs 12 of a suitable shape memory material. If a temperature responsive shape memory material such as nitinol is used, transition between the martensitic and austenitic states of the material can be achieved by temperature transitions relative to a transition temperature. In the martensitic state, the material softens, thereby permitting a filter formed thereof to be compressed and loaded into a catheter. If the transition temperature of the material is set at, or near to normal body temperature, then the filter legs will pass to the austenitic state when the filter is ejected from the catheter and expand to regain a memorized shape.

Figure 3:
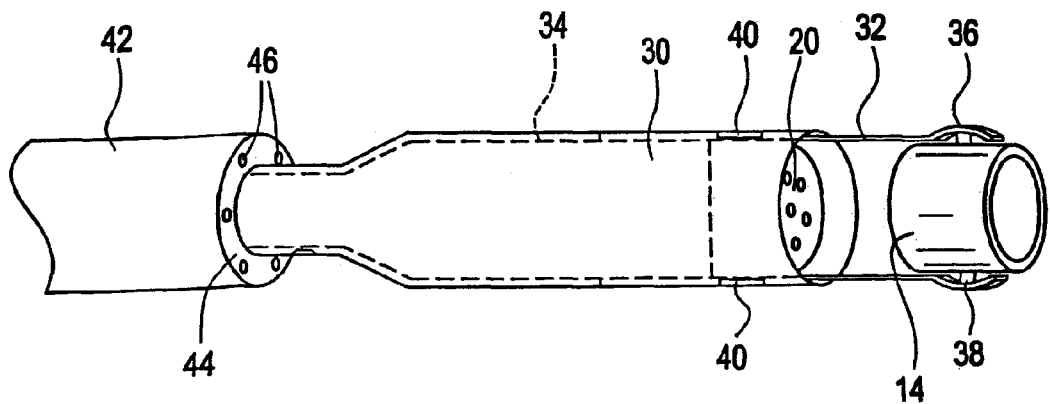
FIG. 3 is a perspective view showing the locking sleeve for the leg retention sleeve of FIG. 2.

For delivery through the catheter 22, the leg retention sleeve 14 is locked to the anchor support hub 20 by a locking sleeve 30 which surrounds both the anchor support hub and the leg retention sleeve when in the locking position as shown in FIG. 1. In the unlocked position, the locking sleeve is moved longitudinally back away from the leg retention sleeve as shown in FIG. 3. Two spring arms 32 are connected at one end to a housing 34 behind the anchor support hub and extend outwardly over opposite sides of the leg retention sleeve. The free end of each of the spring arms is curved to form an arcuate latch member 36 which overlies and, in the locking position of FIG. 1, engages a locking projection 38 formed on the leg retention sleeve. When the locking sleeve 30 moves toward the locking position over the leg retention sleeve 14, it forces the spring arms 32 and 34 together and the arcuate latch members engage the locking projections. As the locking sleeve reaches the full locking position of FIG. 1, the arcuate latch members slide into slots 40 in the locking sleeve and the leg retention sleeve is positively locked to the anchor support hub. However, as the locking sleeve is moved longitudinally away from the leg retention sleeve, the arcuate configuration of the latch members 36 permits them to slip out of the slots 40, and as the locking sleeve moves further, the spring arms 32 move outwardly causing the arcuate latch members to disengage the locking projections 38.

The locking sleeve 30 is mounted for movement toward and away from a centering shaft 42 which extends from a distal end 44 adjacent to the vena cava filter 10 back to the entry end of the catheter 22. The distal end of the centering shaft is formed with a plurality of spaced lumens 46, each of which mounts one of a plurality of centering arms 48. The centering shaft moves these centering arms out of the catheter 22 behind the vena cava filter, and these centering arms then expand outwardly to engage the vessel wall and center the leading end of the filter. These centering arms can be formed of spring metal or plastic, but are preferably formed of shape memory material such as nitinol.

To control the positioning of the vena cava filter 10 and subsequent ejection of the anchors 28 from the second open ends of the legs 12, an elongate drive shaft 50 extends from the entry or proximal end 52 of the catheter 22 through the catheter to a releasable connection 54 with the anchor support hub 20. This releasable connection can be any suitable connection which facilitates release of the drive shaft from the anchor support hub by manipulation of the drive shaft at the proximal end of the catheter such as a threaded connector as shown, a hook and eye connector, engaging hook connectors, and known twist engagement and release connectors. This drive shaft passes through the centering shaft 42 and is both rotationally and longitudinally movable relative thereto.

Figure 4:
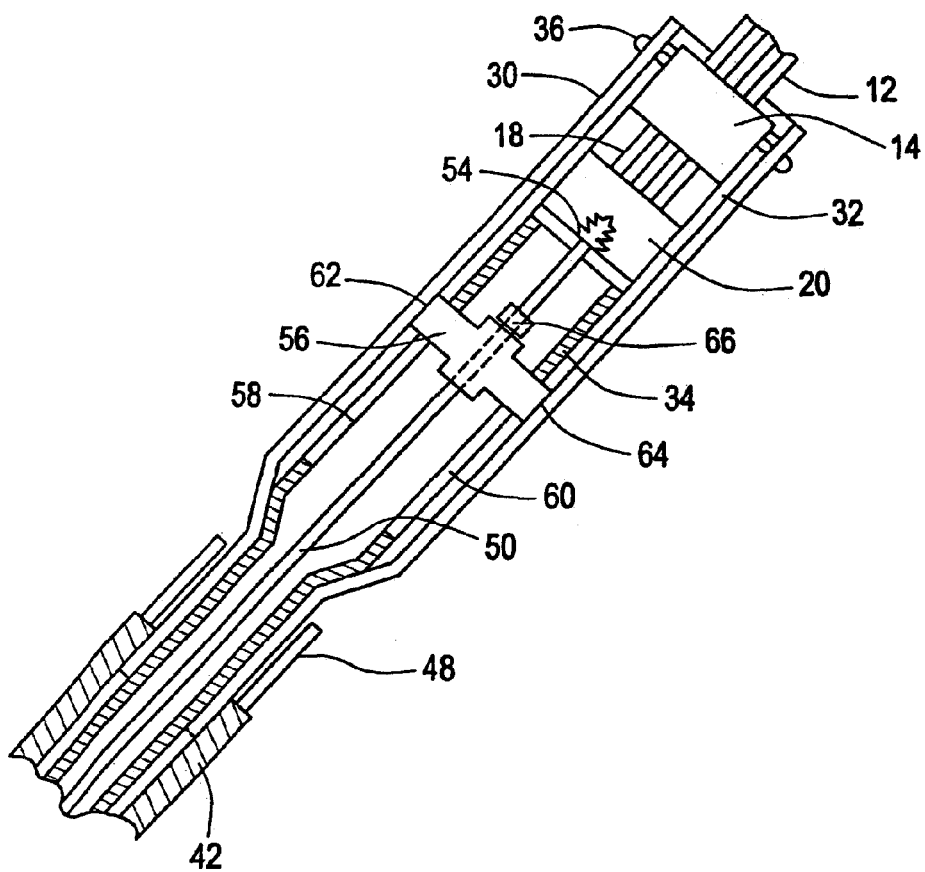
FIG. 4 is a sectional view showing the operating mechanism for the locking sleeve and anchor support hub of FIG. 1.

As shown in FIG. 4, the drive shaft passes through and is both rotationally and longitudinally movable relative to a locking sleeve operator 56 which passes through slots 58 and 60 in the housing 34. The locking sleeve operator is secured at 62 and 64 to the locking sleeve 30 and operates to move the locking sleeve away from the leg retention sleeve 14 as the locking sleeve operator moves away from the leg retention sleeve in the slots 58 and 60. The drive shaft operates to move the locking sleeve from the locked position by means of a stop 66 secured to the drive shaft and positioned to engage the locking sleeve operator.

When the catheter 22 reaches a desired position within a blood vessel, the vena cava filter 10 and centering arms 48 are exposed by either ejecting them from the catheter or drawing the catheter back from around them. Now the elongate legs 12 and centering arms 48 will expand outwardly into engagement with the vessel wall. However, the anchors 28 will remain enclosed within the elongate legs, and this permits the vena cava filter to be moved relative to the blood vessel after expansion of the elongate legs until an exact position is attained. If a substantial position change is required, the centering arms and vena cava filter can be drawn back into the catheter and subsequently redeployed in a new position.

Figure 5:
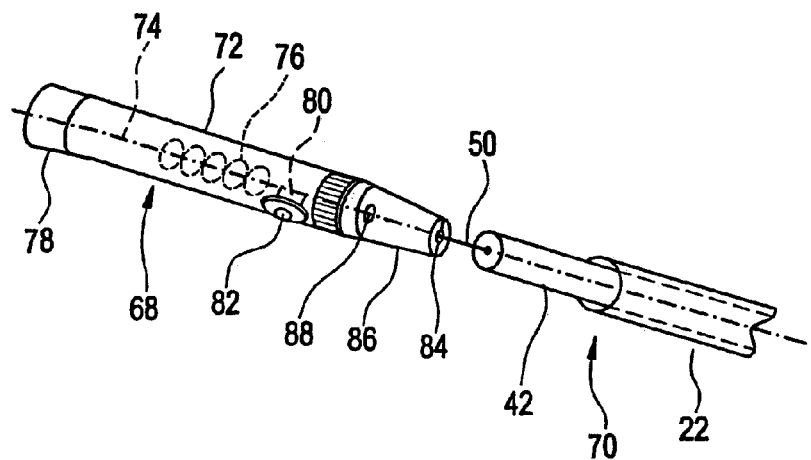
FIG. 5 is a perspective view showing a spring powered triggering unit at the proximal end of the catheter of FIG. 1 for propelling the anchor support hub.

With the vena cava filter in the desired position within a blood vessel and the elongate legs 12 engaging the vessel wall, the anchors 28 are now positively ejected out from the second open ends 26 of the elongate legs so as to penetrate through the vessel wall. To achieve this positive ejection of the anchors subsequent to engagement of the elongate legs with the vessel wall with sufficient force to result in penetration of the vessel wall, the drive shaft 50 is connected to a triggering unit 68 at the proximal or entry end 70 of the catheter 22. This triggering unit can be formed by a number of known units capable of imparting a longitudinal force to the drive shaft. An electrically powered solenoid unit can be used for this purpose as well as a number of spring powered units. In FIG. 5, the triggering unit is formed by a conventional ballistic-type lancer of the type commonly used to cause a needle to puncture a patient's skin to provide a blood sample. Such lancers include a hollow body 72 which contains a plunger 74 capable of moving axially back and forth within the body. The plunger is surrounded by a coil spring 76 which becomes compressed when the plunger is pulled back and armed by an end knob 78. The armed plunger is held in place by a trigger 80 which is activated to release the plunger by a button 82. When the plunger is released, the coil spring 76 propels the plunger toward an opening 84 in a nose cap 86 attached to the hollow body. For normal use of the ballistic type lancer, a needle is secured to the end 88 of the plunger and is propelled by the released plunger out through the opening 84 and into the skin of a patient. In FIG. 5, the drive shaft 50 is secured to the end 88 of the plunger, and when the armed plunger is released, the drive shaft is propelled longitudinally to drive the anchor support hub 20 toward the leg retention sleeve 14. This causes the long shafts 18 to move longitudinally through the elongate legs 12 to propel the anchors out and through the vessel wall. FIG. 6 illustrates an expanded vena cava filter 10 with the anchors 28 in the configuration that they would assume after passing through the vessel wall. The structure and operation of these anchors will be subsequently described.

A significant advantage of the vena cava filter 10 is that it can be repositioned even after the anchors are in place without the necessity to withdraw the complete filter back into the catheter 22. So long as the elongate legs are in contact with the vessel wall, the anchors 28 can be withdrawn from the vessel wall and back into the elongate legs by causing the drive shaft 50 to move the anchor support hub 20 away from the leg retention sleeve 14. Now the vena cava filter can be repositioned, the plunger 74 of the triggering unit 68 can be rearmed, and the anchors can again be ejected to pierce the vessel wall.

Once the vena cava filter 10 is properly positioned and anchored within a blood vessel, the drive shaft 50 is disconnected from the anchor support hub 20 and is pulled away from the anchor support hub causing the stop 66 to engage and move the locking sleeve operator 56 away from the anchor support hub. This results in movement of the locking sleeve 30 away from the leg retention sleeve 14 so that the spring arms 32 spring outwardly and the latch members 36 disengage from the locking projections 38. Now the centering shaft 42, locking sleeve 30, drive shaft 50 and housing 34 may be drawn back through the catheter 22 leaving the vena cava filter in place within the blood vessel.

To subsequently remove a previously anchored vena cava filter, standard body retrieval devices which engage the filter body may be used. For example, a hook to be engaged by a retrieval device can be attached to the anchor support hub 20.

The anchors 28 are formed at the proximal ends of the long anchor shafts 18, and within the elongate legs 12 the anchors assume the same configuration as the shafts with which they are integrally formed. The shafts conform in configuration to the internal configuration of the elongate legs so as to easily move longitudinally within the elongate legs, and usually the shafts will be cylindrical with a pointed end which forms the leading end of the anchor. An enlarged view of the anchor of FIG. 6 is shown in FIG. 7.

Figure 7:
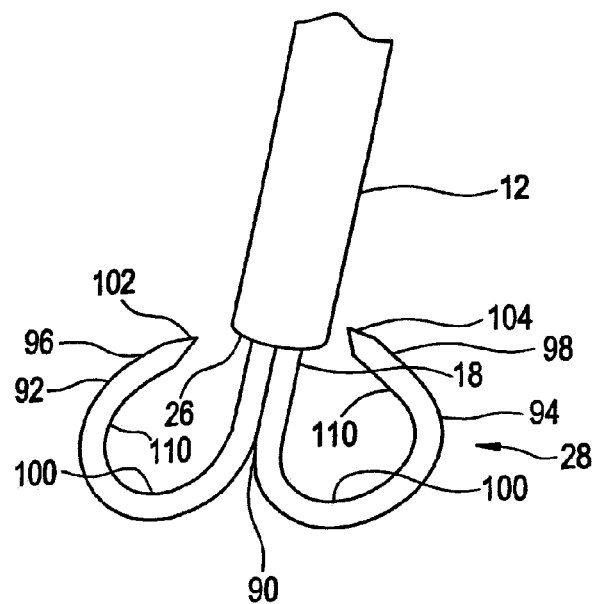
FIG. 7 is a perspective view of a deployed anchor for the blood clot filter of FIG. 6.

Referring to FIG. 7, the tubular anchor shaft 18 is split down the center at 90 to form the opposed arms 92 and 94 of the anchor. The inner surfaces 96 and 98 of each of the arms is flat while the remaining surface 100 of each arm is arcuate, so that when the inner surfaces of the arms are contacting, a straight tubular end section is formed on the end of each long shaft 18. The pointed end of each long shaft forms the pointed ends 102 and 104 on the arms 92 and 94 of the anchor.

The expanded shape memory configuration of the anchors 28 is shown in FIGS. 6 and 7. Each anchor with the inner surfaces 96 and 98 in contact is ejected from an elongate leg 12 in a straight configuration when the anchor support hub 20 is driven toward the leg retention sleeve 14. The pointed lead end of each anchor will pierce the wall of a blood vessel so that the entire anchor passes through the vessel wall, at which point the anchor expands to its shape memory configuration shown in FIG. 7. Now the end 26 of the elongate leg engages the inner surface of the blood vessel wall while the pointed ends 102 and 104 of the arms 92 and 94 engage the outer surface of the blood vessel wall. It is important to note that portions of the expanded anchor, in this case the arms 92 and 94, extend outwardly on opposite sides of the shaft 18 so that forces in either direction in the plane of the anchor arms will not dislodge the anchor in the manner which can occur with a single hook which extends outwardly in only one direction from a support shaft. To provide additional protection from accidental dislodgement, the anchors 28 are oriented as shown in FIG. 7 so that the opposed arms 92 and 94 of the anchor expand transversely to the longitudinal direction 106 of blood flow through the filter 10. Thus the forces created by direct or reverse blood flow cannot dislodge the anchor, but since the anchor arms are each formed from half of a shaft 18 of a very small diameter, a withdrawal force along the longitudinal axis of the shaft will permit the anchor arms to come together to facilitate anchor withdrawal from the vessel wall.

It is important to note that the anchor arms 92 and 94 curve outwardly and back toward the shaft 18 to engage the outside surface of the vessel wall. This causes the anchor to be loaded in compression against the vessel wall when forces normal to the longitudinal axis of the vessel are applied to a medical device attached to the anchor. This compression aspect greatly enhances the anchoring function provided by the anchor and facilitates the effective use of very small, fine anchor components.

Figure 8:
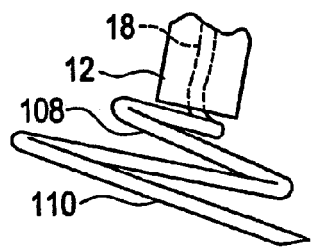
FIG. 8 is a perspective view of a second embodiment of a deployed anchor of the present invention.

The anchors 28 may take a number of forms so long as the anchor expands from a straight configuration from within an elongate leg 12 to a shape memory configuration where the anchor extends outwardly on at least two opposite sides of the shaft 18. In FIG. 8, the anchor 28 expands to a spiral configuration so as to extend completely around the shaft 18. Here the shaft is not split as shown in FIG. 7, but instead the intact end of the shaft is used to form the spiral 108. In all cases, first end of the anchor to emerge from an elongate leg 12 is a straight section 110 bearing the anchor point, and this section passes through a blood vessel wall before following sections which will form curves emerge. Both the anchors of FIGS. 7 and 8 tend to flatten by spring action against the vessel wall after expanding.

To form the anchor 28 of FIG. 9, the shaft 18 is flattened at the end and split at 90 to form two opposed, flat arms 112 and 114 which expand outwardly on opposite sides of the shaft. These arms emerge from the elongate leg 12 as a straight section which passes through the vessel wall and then splits and bends outwardly at 116 and 118 to form the arms. These arms lie against the outer surface of the vessel wall and in a vena cava filter, are oriented transverse to the longitudinal direction of blood flow through the filter.

For some medical applications, a need has arisen for a single anchor to tether a device within a body vessel or to a body wall. An apparatus similar to that previously described with reference to the multiple anchor vena cava filter 10 can be employed to deploy the single anchor 120 of FIG. 10. The single anchor 120 is formed at the distal end of an anchor shaft 122 mounted in an elongate tube 124, Both the shaft 122 and the tube 124 are formed of shape memory material as described relative to the elongate legs 12 and long shafts 18, but are normally much shorter in length than the elongate legs and shafts 18. A tube retention sleeve 126 retains the single tube 124 in the same manner that the leg retention sleeve 14 operates to retain the elongate legs 12, and this tube retention sleeve is engaged by a locking sleeve (not shown) and spring arms 32 operative in the manner previously described. A drive shaft 50 is connected at the entry end of the catheter 22 to a triggering unit 68, and is also connected to a releasable connection 128 similar to the releasable connection 54. This releasable connection is firmed in a shaft support hub 130 normally spaced from the tube retention sleeve 126 which is connected to the proximal end of the anchor shaft.

The drive shaft 50 is movable in a control shaft 132 similar to the centering shaft 42 which operates to move the shaft support hub and tube retention sleeve longitudinally to expel the tube 124 containing the anchor 120 from the catheter 22. The tube 124 will now assume a predetermined shape to position the anchor relative to a body wall which will receive the anchor. Now the triggering unit 68 can be operated to cause the drive shaft 50 to move the shaft support hub 130 toward the tube retention sleeve 126 to drive the anchor 120 through the body wall. The anchor 120 is formed of shape memory material and can take the form and operate in the manner of any of the anchors previously described. Once the anchor is delivered, the spring arms 32 can be operated to release the tube retention sleeve 126, and the drive shaft can be released from the releasable connection 128 so that the drive and control shafts, and in some cases the catheter, can be withdrawn. If the purpose of the anchor is to anchor the catheter in position, then a tether 134 is provided between the catheter and the anchor, and the catheter will not be withdrawn with the drive and control shafts.

In some instances, the catheter 22 may be a dual lumen catheter having a first lumen 136 containing the described anchor mechanism and a second lumen 138 containing an in implantable medical device 140 to be anchored by the anchor 120. In this case, a tether 142 is connected between the anchor and the implant able medical device, and once the anchor is in place, the implantable medical device is ejected from the catheter.

When it is possible to use the catheter to properly position the anchor 120 relative to a body wall, the tube 124 and tube retention sleeve 126 can be eliminated and replaced by the catheter lumen. Now the drive shaft 50 will drive the shaft support hub 130 longitudinally to drive the anchor from the catheter lumen and through the body wall.

Figure 11:
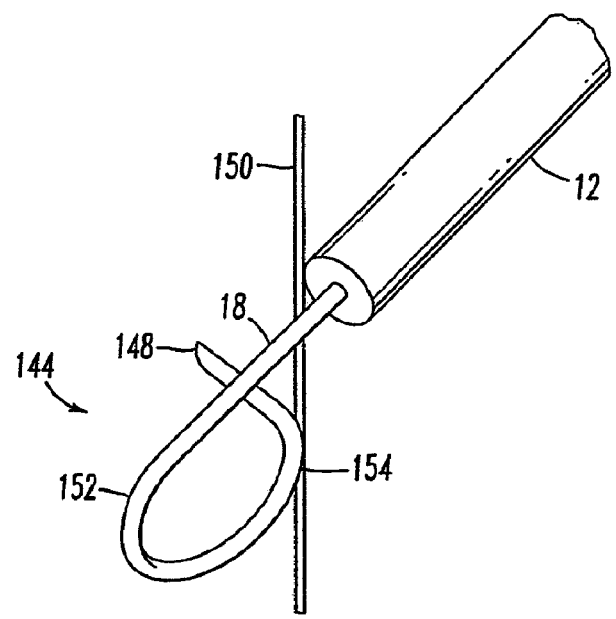
FIG. 11 is a perspective view of a fourth embodiment of a deployed anchor of the present invention which deploys to form a closed loop having a wall engaging section which crosses over and extends beyond the anchor shaft.
Figure 12:
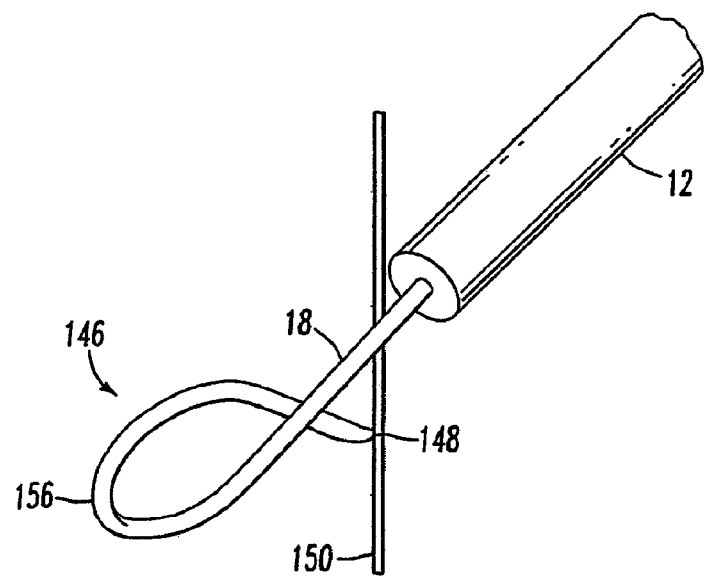
FIG. 12 is a perspective view of a fifth embodiment of a deployed anchor of the present invention which deploys to form a closed loop having a wall engaging section which crosses under and extends beyond the anchor shaft.

FIGS. 11 and 12 show anchors 144 and 146 respectively which each form a single, closed loop in the expanded shape memory configuration. Each of the anchors 144 or 146 is ejected from an elongate leg 12 in a straight configuration coextensive with the long anchor shaft 18 when the anchor support hub 20 is driven toward the leg retention sleeve 14. The end of each anchor, which may be pointed as indicated at 148, will pierce the wall 150 of the vessel containing the vena cava filter 10 or other medical implant device to be anchored, so that the entire anchor passes through and expands against the outer surface of the vessel. In its shape memory expanded configuration, the anchor 144 extends arcuately outwardly from the anchor shaft and loops back to cross over and extend beyond the anchor shaft to form a single closed loop 152. The loop 152 engages the outer surface of the vessel wall 150 at 154 and is loaded in compression against the vessel wall; a compression which increases in response to forces applied in any direction which tend to force the loop 152 further against the vessel wall. As these forces increase, the loop 152 changes configuration and decreases in size becoming more rigid as a greater portion of the loop is forced across the anchor shaft 18, thereby increasing the anchoring force of the anchor.

Unlike the anchor 144 which is oriented to be confined in the angular space between the anchor shaft 18 and the vessel wall 150, the anchor 146 is oriented to be outside this angular space. This anchor in its shape memory expanded configuration extends arcuately outwardly from the anchor shaft and loops back to cross under and extend beyond the anchor shaft to form a single closed loop 156 which is loaded in compression against the vessel wall. However, due to the orientation and configuration of the anchor 146, as forces on the anchor increase, the loop straightens rather than decreasing in size and may be withdrawn with less force than that required to withdraw the anchor 144.

Both the anchors 144 and 146 can be configured to provide a double looped anchor by splitting the shaft 18 and forming double, opposed closed loops similar to the open loops formed by the arms 92 and 94 of FIG. 7. However both the double closed loops of the modified anchors 144 and 146 would extend arcuately back over or under the anchor shaft in the manner shown by FIG. 11 or 12.

It may be desirable to insure that the distal end 24 of an anchor containing filter leg 12 cannot follow an ejected anchor through the sidewall of a blood vessel once the anchor is deployed. This can be accomplished in accordance with this invention by forming a side opening in the portion of the filter leg which will contact the vessel wall with this side opening being spaced above the distal end of the filter leg. The anchor is then ejected through this side opening laterally of the filter leg once the filter leg has expanded into contact with the vessel wall. The anchor will now pass through the vessel wall at a point above the distal end of the filter leg thereby positively precluding the distal end of the filter leg from following the anchor through the vessel wall.

Figure 13:
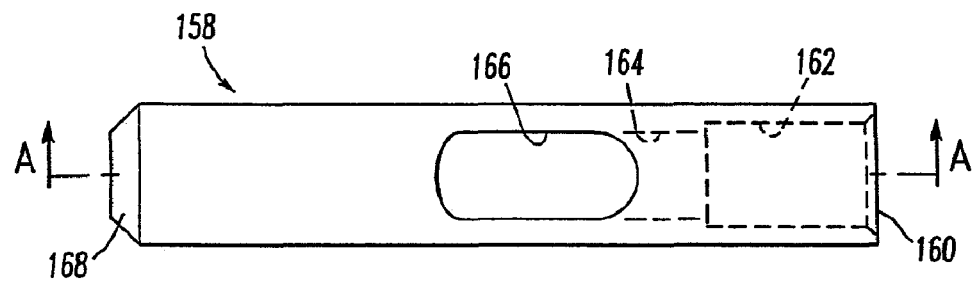
FIG. 13 is a view in side elevation of an anchor guide boot which is secured to the end of an anchor containing blood clot filter leg.
Figure 14:
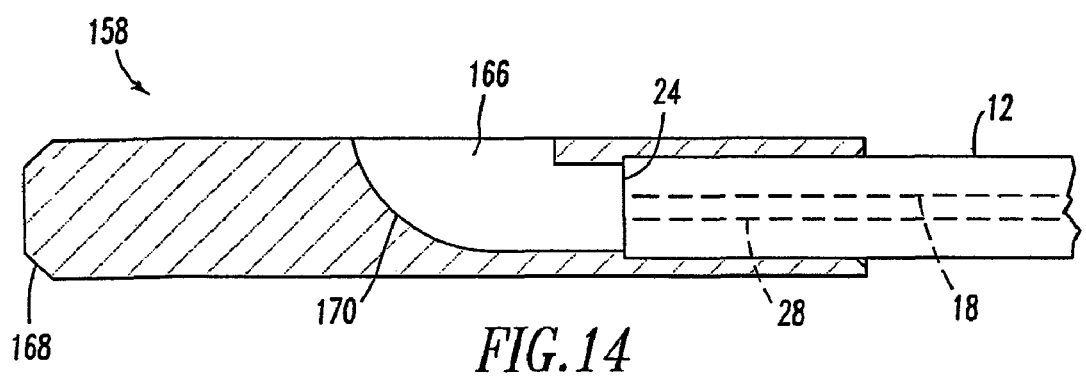
FIG. 14 is a sectional view of the anchor guide boot of FIG. 13.
Figure 15:
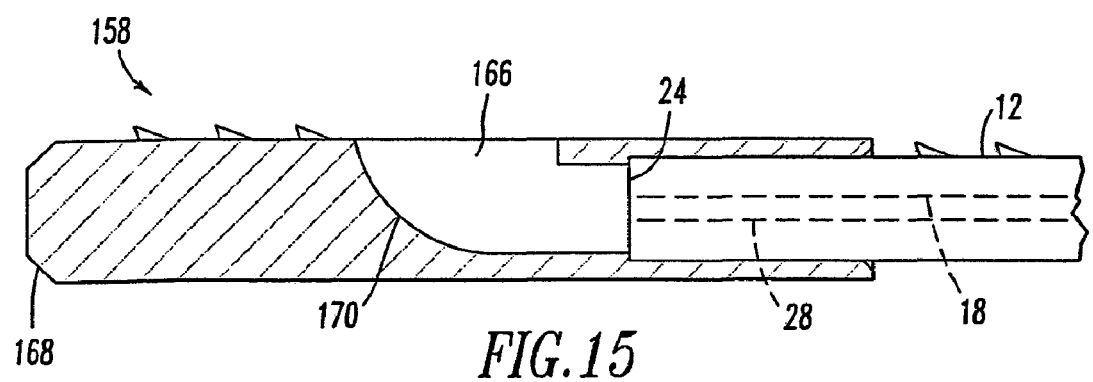
FIG. 15 is a sectional view of a modification of the anchor guide boot of FIG. 14.

It has been found to be advantageous to attach a separate anchor guiding boot 158 of the type shown in FIGS. 13, 14 and 15 to the distal end 24 of each anchor containing filter leg. The anchor guiding boot has an open end 160 which opens into an internal seat 162 for the distal end of the filter leg. The end of the filter leg may be secured within the seat 162 by any known means such as by a friction fit, welding, heat expansion or bonding. An internal passage 164 connects the seat 162 to a side opening 166 formed in the anchor guiding boot, and this side opening is spaced from the closed end 168 of the anchor guiding boot. The internal passage is closed by a curved, guidewall 170 which curves upwardly from the lower end of the opening 166 to the opposite side of the internal passage.

When the triggering unit 68 is activated, each of the long anchor shafts 18 move an anchor 28 toward the closed end 168 of an anchor guiding boot 158 and into engagement with the curved, guidewall 170 which closes the internal passage 164. The anchor is then guided along the curved, guidewall. causing the shaft 18 to bend as the anchor is ejected out through the side opening 166 and laterally through the wall of the blood vessel. The anchor guiding boot 158 may be formed of tantalum to provide high feasibility under fluoroscopy.

To prevent longitudinal movement of a filter leg 12 relative to the blood vessel caused by the force applied to the curved, guidewall 170 by the ejecting anchor 28, barbs 172 may be formed on either the anchor guiding boot 158, the filter leg 12 or both. These barbs engage the blood vessel wall when the filter leg contacts the vessel wall, and are inclined to penetrate and prevent longitudinal movement of the filter leg toward the closed end 168 of the anchor guiding boot.

Figure 16:
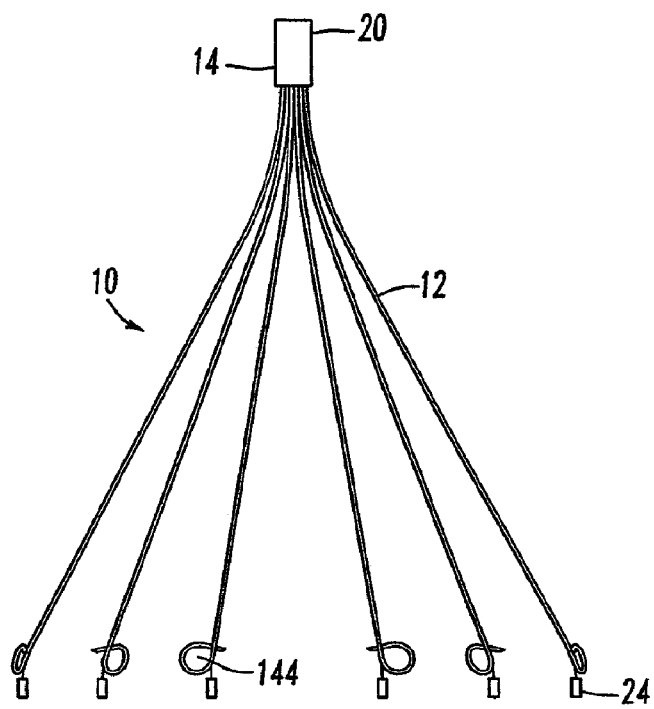
FIG. 16 is a perspective view of a deployed blood clot modified to eject anchors from the side of the filter legs above the distal ends of the legs with the anchors deployed.
Figure 17:
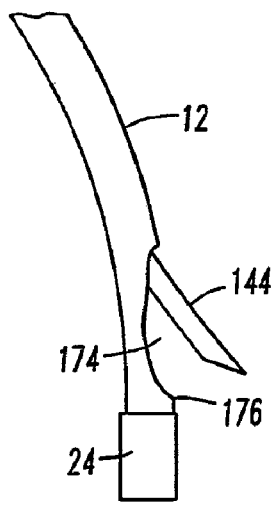
FIG. 17 is a view in front elevation of an end section of a filter leg of the filter of FIG. 16 with an anchor partially deployed.
Figure 18:
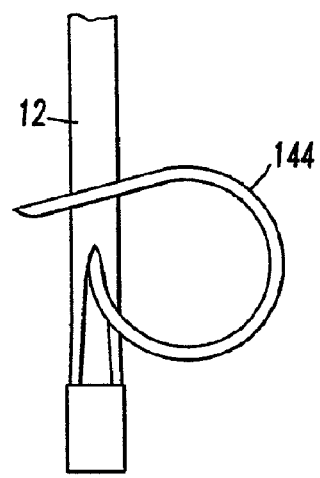
FIG. 18 is a view in front elevation of an end section of a filter leg of the filter of FIG. 16 with an anchor fully deployed.

To eliminate the need for the anchor guiding boot 158, a side opening 174 to facilitate lateral anchor ejection when the triggering unit 68 is activated can be formed directly in a filter leg 12 and spaced above the distal end 24 thereof as shown in FIGS. 16-18. The tubular filter leg is closed between the lower end of the side opening 174 and the distal end of the filter leg so that the anchor will be ejected laterally of the filter leg through the side opening. This closure may be formed by a curved wall 176 which curves upwardly from the lower end of the side opening across the tubular interior of the filter leg. The filter 10 of FIG. 16 is shown in the expanded configuration with the anchors 144 deployed laterally through the side openings 174. FIG. 17 shows this anchor partially deployed, while FIG. 18 shows this anchor fully deployed.

What is claimed is:

1. A method for securing a medical device within a lumen, comprising:
    positioning the medical device within the lumen so as to place a distal end of a hollow leg of the medical device against an inner surface of a wall of the lumen;
    advancing an anchor from a stowed configuration within the hollow leg, through an opening in the hollow leg such that an anchor tip completely penetrates through the wall of the lumen from the inner surface to an outer surface; and
    continuing to advance the anchor through the opening until the anchor reaches a deployed configuration, wherein, an anchor portion proximal to the anchor tip forms a closed loop that is entirely positioned outside of the wall.

2. The method of claim 1, wherein the anchor is substantially straight when in the stowed configuration.

3. The method of claim 1, wherein, when in the deployed configuration, the anchor portion proximal to the anchor tip extends arcuately toward the outer surface and the anchor tip extends away from the outer surface.

4. The method of claim 1, wherein, when in the deployed configuration, the anchor portion proximal to the anchor tip extends arcuately away from the outer surface and a tip of the anchor extends toward the outer surface.

5. The method of claim 1, wherein, in response to a force applied to the medical device, the closed loop decreases in diameter.

6. The method of claim 5, wherein the force applied to the medical device results from expansion of the lumen.

7. The method of claim 1, wherein extending the anchor through the opening comprises extending the anchor laterally through the opening.

8. The method of claim 1, wherein a part of the anchor portion proximal to the anchor tip is adjacent to the outer surface when the anchor is in the deployed configuration.

9. The method of claim 1, further comprising compressing the closed loop against the outer surface such that the wall is caught between the closed loop and the hollow leg.

10. A method for deploying a medical device in a vessel, wherein the medical device includes hollow leg having an opening proximal to a distal end of the hollow leg, an elongate anchor shaft disposed within the hollow leg, and an anchor at a distal end of the anchor shaft, the anchor having a proximal anchor portion attached to the anchor shaft, a central anchor portion adjacent to the proximal anchor portion, and a tip at the distal end of the anchor adjacent to the central anchor portion, the method comprising:
    advancing the anchor relative to the hollow leg so the anchor distal tip passes through the opening in the hollow leg;
    penetrating a vessel wall with the anchor tip;
    further advancing the anchor relative to the hollow leg until the central anchor portion is outside of the vessel wall; and
    curving the central anchor portion such that the tip crosses over and extends beyond the proximal anchor portion to form a closed loop positioned entirely outside of the vessel wall.

11. The method of claim 10, wherein advancing the anchor relative to the hollow leg comprises extending the anchor laterally from the hollow leg.

12. The method of claim 10, wherein the central anchor portion comprises a shape-memory material, and wherein curving the central anchor portion comprises returning the central anchor portion to a pre-shaped form.

13. The method of claim 10, wherein curving the central anchor portion comprises curving the central anchor portion arcuately toward an outer surface of the vessel wall such that the tip of the anchor extends away from the outer surface.

14. The method of claim 10, wherein curving the central anchor portion comprises curving the central anchor portion arcuately away from an outer surface of the vessel wall such that the tip of the anchor extends towards the outer surface.

15. The method of claim 10, wherein the closed loop decreases in diameter in response to a force applied to the medical device.

16. The method of claim 15, wherein the force applied to the medical device results from expansion of the lumen.

17. The method of claim 10, wherein curving the central anchor portion comprises placing a part of the closed loop adjacent to an outer surface of the vessel wall.

18. The method of claim 10 further comprising compressing the closed loop against the outer surface such that the vessel wall is caught between the closed loop and the hollow leg.

19. The method of claim 1, wherein continuing to advance the anchor comprises advancing the anchor until the anchor portion proximal to the anchor tip engages the outer surface.

* * * * *